United States Patent
Liou (10) Patent No.: US 8,485,817 B2
(45) Date of Patent: Jul. 16, 2013

(54) ORTHODONTIC DEVICE

(76) Inventor: Jein-Wein Liou, Taipei (TW)

( * ) Notice: Subject to any disclaimer, the term of this patent is extended or adjusted under 35 U.S.C. 154(b) by 0 days.

(21) Appl. No.: 12/924,296

(22) Filed: Sep. 23, 2010

(65) Prior Publication Data

US 2012/0077139 A1    Mar. 29, 2012

(51) Int. Cl.
*A61C 3/00*    (2006.01)

(52) U.S. Cl.
USPC ............................................. 433/20

(58) Field of Classification Search
USPC .......................................... 433/8, 10, 18, 20
See application file for complete search history.

(56) References Cited

U.S. PATENT DOCUMENTS

| | | | |
|---|---|---|---|
| 3,838,515 A * | 10/1974 | Paugh et al. | 433/20 |
| 5,683,245 A * | 11/1997 | Sachdeva et al. | 433/20 |
| 6,431,861 B1 * | 8/2002 | White | 433/20 |
| 2002/0110772 A1 * | 8/2002 | Abels et al. | 433/10 |

* cited by examiner

*Primary Examiner* — Sunil K Singh (57) ABSTRACT

An orthodontic device includes a generally U-shaped metal wire whose two ends are at different vertical heights and which therefore has a 3-dimensional recumbent S shape in front view. The U-shaped metal wire is secured, by an elastic band or a cover, to each of a plurality of orthodontic brackets cemented respectively to a patient's teeth, and due to the difference of height between the two ends of the U-shaped metal wire, a resilient restoring force is generated to individually adjust the row of teeth on the upper or lower jaw to the normal heights and thereby correct the occlusal cant and craniofacial anomalies.

8 Claims, 9 Drawing Sheets

ORTHODONTIC DEVICE

BACKGROUND OF INVENTION

1. Field of the Invention

The present invention relates to orthodontic devices and, more particularly, to an orthodontic device capable of individually adjusting the row of teeth on the upper or lower jaw to the normal tooth positions by means of a resilient restoring force resulting from a height difference between the two ends of a U-shaped metal wire.

2. Description of the Prior Art

Orthodontics is a branch of dentistry that provides a variety of treatments for people who suffer from malocclusion or who are not satisfied with their looks because of tooth irregularity, disproportionate jaw relationships, or both. Malocclusion may result from congenital maxillary/mandibular hyperplasia or hypoplasia, tooth abnormalities, or a size mismatch between the teeth and the dental arches. The various conditions of malocclusion include crowding of teeth, crossbite, forward or backward projection of teeth, excessive spacing between teeth, tooth impaction, misalignment of teeth due to congenitally missing teeth or supernumerary teeth, and so on. Bad oral habits may also lead to such malocclusion problems as openbite, crossbite, and a narrow upper dental arch.

Therefore, orthodontic devices are designed to improve the abnormal development of facial bones, rearrange misaligned teeth, and thereby achieve the following therapeutic purposes:

1. To restore mastication function and thereby improve digestion and the absorption of nutrients;
2. To facilitate the maintenance of oral hygiene and thereby prevent tooth decay and periodontal diseases;
3. To enhance facial esthetics for higher self-confidence and thereby promote normal character development;
4. To enable correct pronunciation and thereby increase learning efficiency; and
5. To enable proper occlusion and lip closure, thereby preventing dryness of the oral mucosa and enhancing the resistance of the oral cavity against infection.

Orthodontic treatments are generally classified as follows, according to the orthodontic appliances used:

1. Fixed orthodontic brackets: According to the patient's liking, orthodontic brackets made of metal, transparent ceramics, or compounds are cemented to the outer or inner sides of the patient's teeth by an adhesive and serve as a medium for delivering force to the teeth.
2. Removable orthodontic devices: Orthodontic plates are placed in the patient's mouth and can be easily removed for easy maintenance of oral hygiene.
3. Jaw bone correction appliances:
    (1) An extraoral traction appliance is worn on the patient's head to generate a traction force that influences bone growth.
    (2) An intraoral functional orthodontic appliance uses the patient's muscles and biting action to generate an orthodontic force that influences the development of the lower face.

A conventional fixed orthodontic device typically includes a straight orthodontic wire fixed in position by rubber bands to a plurality of orthodontic brackets cemented to the tooth surfaces. Each end of the orthodontic wire is attached via a spring to an orthodontic screw implanted in the alveolar bone, so as for the springs to exert a pulling force and thereby pull the skew or misaligned teeth to the normal positions, with a view to correcting jaw position. However, such a conventional orthodontic device is applicable only to horizontal adjustment (e.g., the correction of crowded teeth, forward- or backward-projecting teeth, excessive spacing between teeth, congenitally missing teeth, etc.) but is not suitable for adjusting an inclined row of teeth caused by a vertically tilting upper or lower jaw.

Besides, installation of the conventional fixed orthodontic devices involves local anesthesia and implantation of orthodontic screws into the alveolar bone where the tooth roots are not located. Moreover, the springs which are used to tighten the orthodontic wire do not have direct corrective effect on the jaw bone. Hence, not only are the installation and removal of the orthodontic devices complicated, but also the patients will have to endure pain and discomfort during the installation and removal processes.

SUMMARY OF INVENTION

The primary objective of the present invention is to provide an orthodontic device for adjusting a patient's teeth to positions capable of normal occlusion, wherein the adjustment is carried out by means of a resilient restoring force generated by a U-shaped metal wire whose two ends have a height difference. Thus, fast, effective, and painless craniofacial correction can be achieved without having to implant screws into the patient's jaw bone.

In order to achieve aforementioned objective, the present invention discloses an orthodontic device which comprises a U-shaped metal wire configured to be installed on a plurality of orthodontic brackets cemented to a row of teeth. The U-shaped metal wire has a left end and a right end located at different vertical heights with respect to a horizontal plane passing lengthwise through the U-shaped metal wire at a middle point thereof. Wherein, after the U-shaped metal wire is installed on the plural orthodontic brackets cemented to the row of teeth, the left and right ends of the U-shaped metal wire are pressed vertically to generate a resilient restoring force for pushing and pulling the row of teeth on an upper jaw or a lower jaw and thereby adjusting the teeth from an inclined alignment to a horizontal alignment.

In a preferred embodiment, the U-shaped metal wire is made of a resilient metallic material, the resilient metallic material being one of stainless steel, iron, titanium, β-titanium, nickel titanium, clear material and a shape memory alloy.

In a preferred embodiment, the greater a vertical distance between the left and right ends of the U-shaped metal wire is, the stronger the resilient restoring force of the U-shaped metal wire will be, and the harder the left and right ends of the U-shaped metal wire will spring back in two opposite directions respectively.

In a preferred embodiment, the U-shaped metal wire and the plural orthodontic brackets on which the U-shaped metal wire is installed are provided on one of outer surfaces and lingual surfaces of the row of teeth.

In a preferred embodiment, the U-shaped metal wire is fixed in position to the plural orthodontic brackets by one of the following: a plurality of rubber bands and a plurality of covers of self-ligation brackets.

In a preferred embodiment, the orthodontic brackets are one of metal orthodontic brackets, ceramic orthodontic brackets, crystal orthodontic brackets, self-ligation brackets and lingual orthodontic brackets, the lingual orthodontic brackets being cemented to the lingual surfaces of the teeth.

In a preferred embodiment, the U-shaped metal wire has a rectangular cross-section and is twisted continuously in the same direction, starting from the middle point of the U-shaped metal wire and proceeding to the left and right ends, such that the cross-section of the U-shaped metal wire is rotated from a horizontal position at the middle point of the U-shaped metal wire to an inclined position at each of the left and right ends, the inclined position having a predetermined angle.

BRIEF DESCRIPTION OF THE DRAWINGS

The structure as well as a preferred mode of use, further objects, and advantages of the present invention will be best understood by referring to the following detailed description of the preferred embodiments in conjunction with the accompanying drawings, in which.

DETAILED DESCRIPTION OF THE PREFERRED EMBODIMENT

Figure 1:
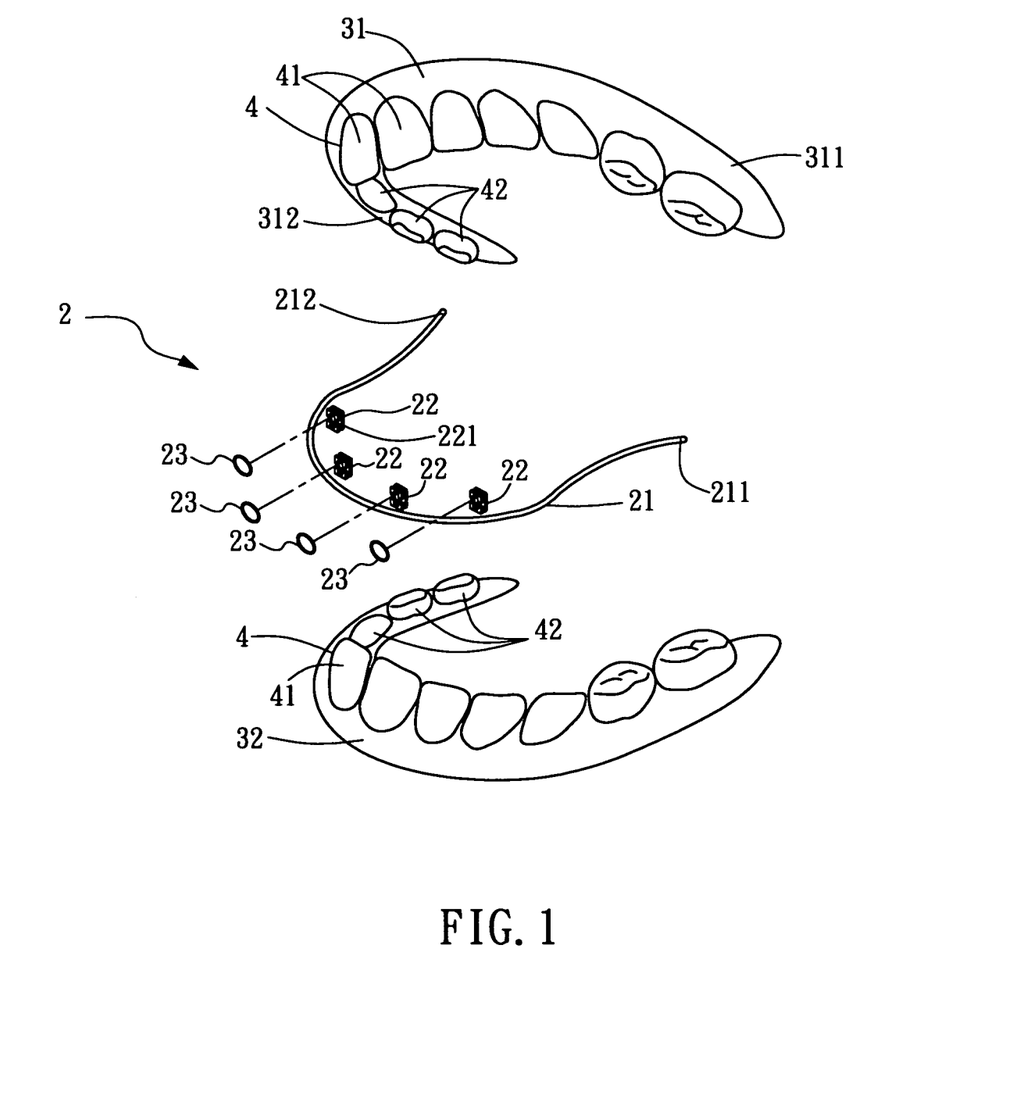
FIG. 1 is an exploded perspective view of an orthodontic device according to a first preferred embodiment of the present invention.
Figure 2:
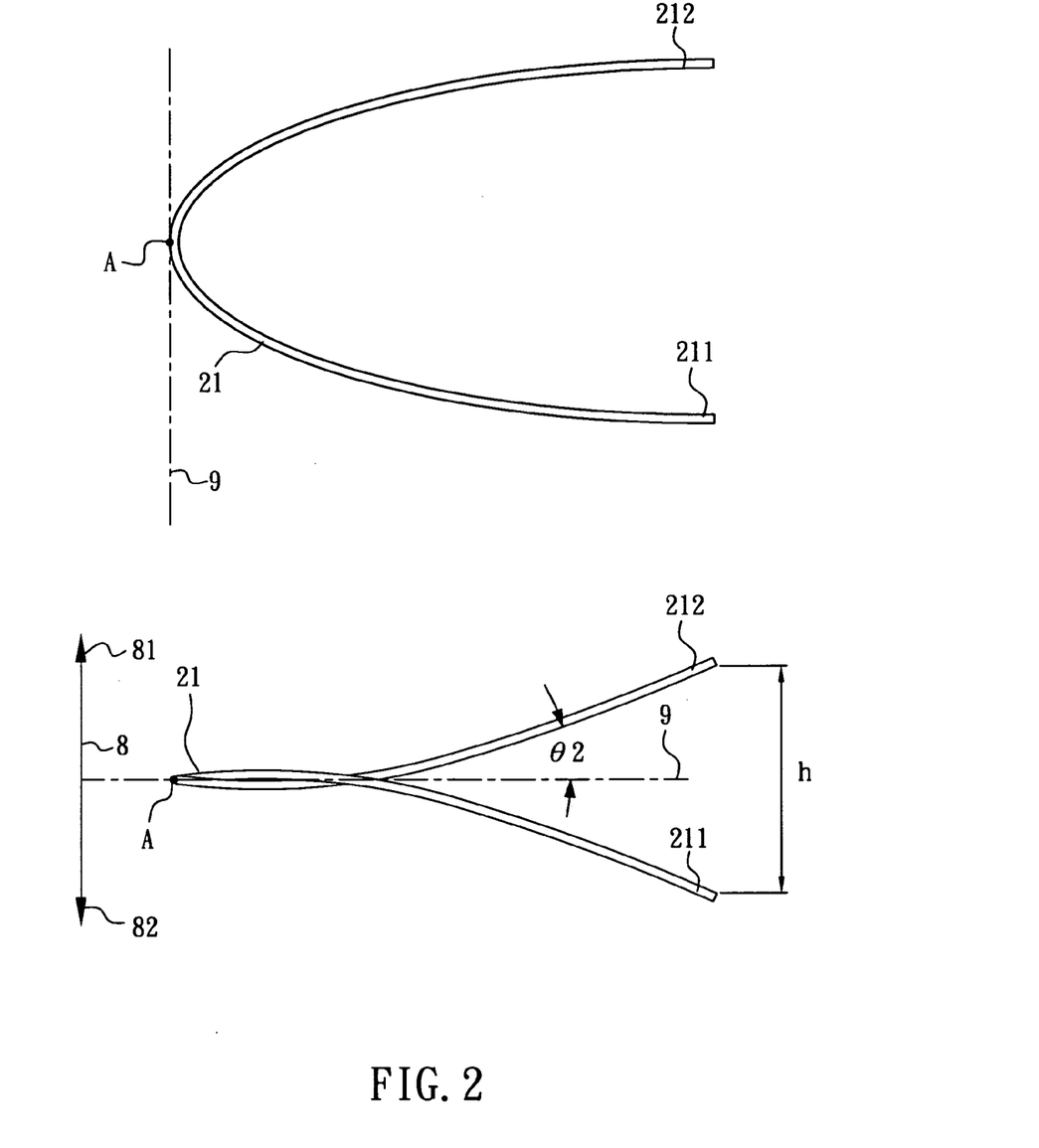
FIG. 2 is a side view and a top view of a U-shaped metal wire of the orthodontic device in the first preferred embodiment of the present invention.
Figure 4:
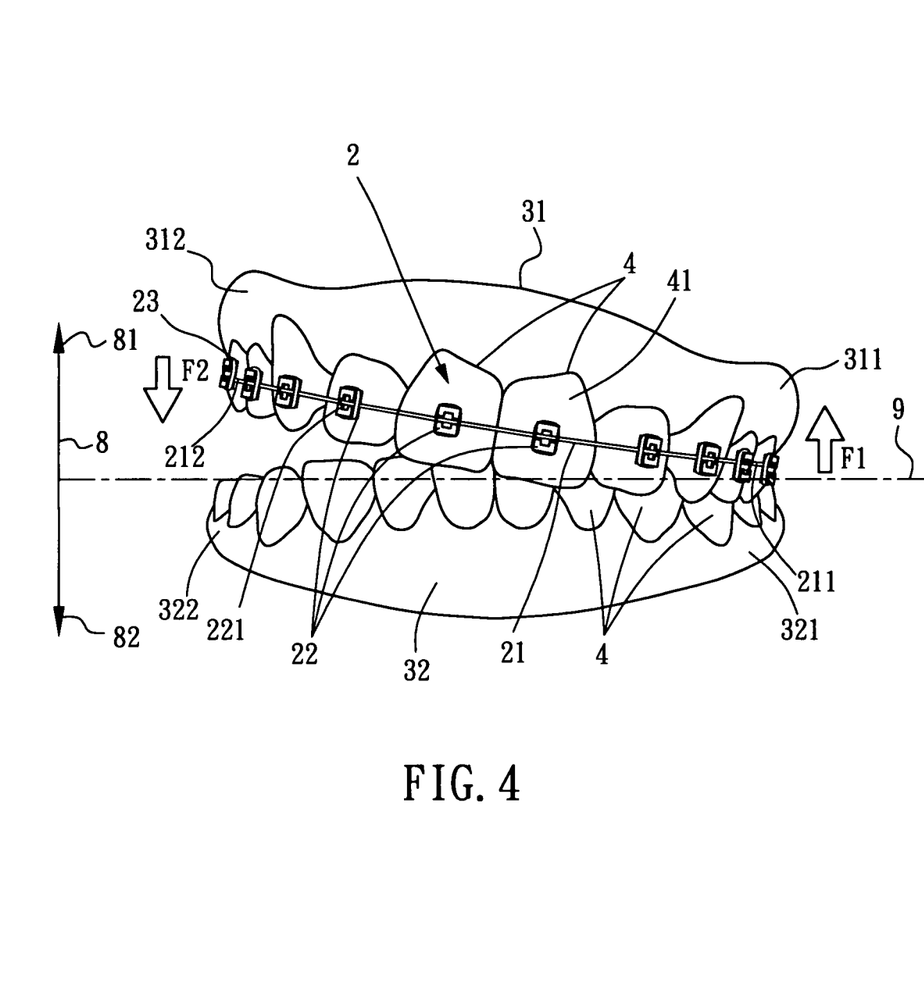
FIG. 4 is a front view of the orthodontic device in the first preferred embodiment of the present invention during correction of the upper jaw.

Referring to FIG. 1 and FIG. 2, an orthodontic device 2 according to a first preferred embodiment of the present invention includes a generally U-shaped metal wire 21, a plurality of orthodontic brackets 22 cemented respectively to the entire row of teeth 4 on an upper jaw 31 or a lower jaw 32, and a plurality of fasteners for securing the U-shaped metal wire 21 in position to the plural orthodontic brackets 22 and thereby preventing the U-shaped metal wire 21 from falling off. In this embodiment, the fasteners are a plurality of rubber bands 23 for setting the U-shaped metal wire 21 in a groove 221 pre-formed on each of the orthodontic brackets 22 cemented to the row of teeth 4, so the U-shaped metal wire 21 will not come off the grooves 211. In another embodiment which is not shown in the figures, the fasteners can also be covers of self-ligation brackets in order to secure the U-shaped metal wire onto the orthodontic brackets. The U-shaped metal wire 21 of the present invention has a left end 212 and a right end 211 which are at different vertical heights with respect to a horizontal plane passing lengthwise through the U-shaped metal wire 21 at its middle point (with the left end 212 being lower than the middle point, and the right end 211 higher than the middle point, in the embodiment shown in FIG. 1). Consequently, the two ends 211, 212 are spaced apart by a vertical distance h (i.e., difference of height). The vertical distance h must be greater than the vertical tilting height of the row of teeth to be corrected (i.e., the difference of height between the left and right ends of the row of teeth). Once the U-shaped metal wire 21 is installed on the plural orthodontic brackets 22, which are cemented to and arranged linearly on the teeth 4, as shown in FIG. 4, the U-shaped metal wire 21 is rendered into a U-shaped curve which lies generally on the same plane and conforms to the positions of the orthodontic brackets 22. As a result, the U-shaped metal wire 21 generates a left-downward, right-upward pushing force due to the resilience of the material of the U-shaped metal wire 21. If the orthodontic device 2 is worn for a sufficiently long time, the long-term left-downward, right-upward pushing force exerted by the U-shaped metal wire 21 will cause the teeth 4 on the upper jaw 31 to displace gradually in a left-downward, right-upward manner, so that even occlusion between the teeth 4 on the upper jaw 31 and the lower jaw 32 can be achieved while the slightly skew face is also adjusted to a more desirable angle.

Figure 3:
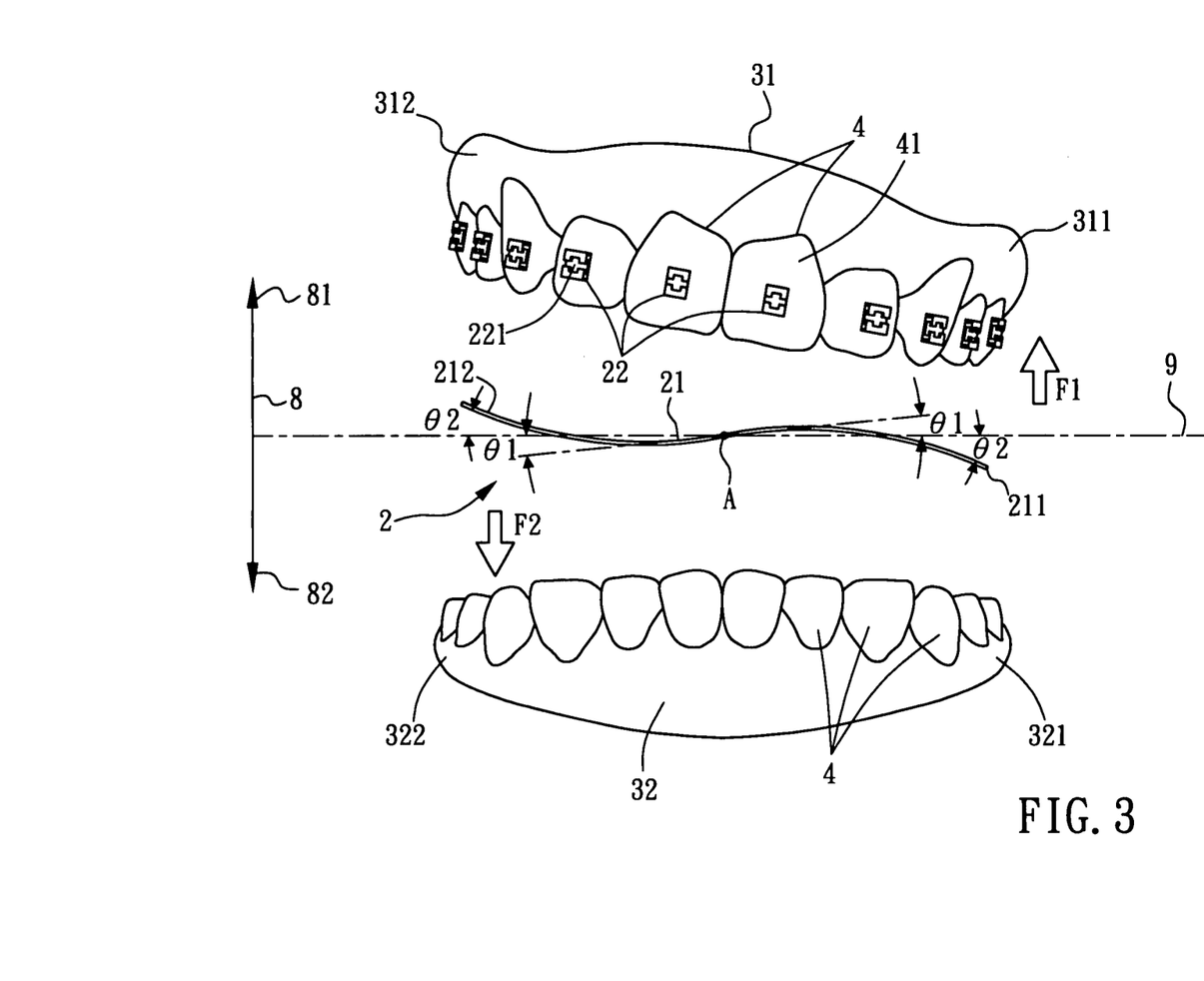
FIG. 3 is an exploded front view of the orthodontic device in the first preferred embodiment of the present invention, wherein the orthodontic device is used to correct an upper jaw.

Reference is now made to FIGS. 2 through 5. As shown in FIG. 2, the orthodontic device 2 in the first preferred embodiment of the present invention defines a horizontal baseline 9 and a vertical baseline 8. The U-shaped metal wire 21 is made of a resilient metal material and, as stated previously, has two ends 211, 212 which are positioned at different vertical heights and spaced apart by the vertical distance h. Referring to FIG. 3 for a front view of the upper and lower jaws 31, 32, the right side 311 of the upper jaw 31 is slightly inclined toward the horizontal baseline 9 such that malocclusion occurs, and consequently a gap is formed (see FIG. 4), between the left side 312 of the upper jaw 31 and the lower jaw 32. As the teeth 4 on the upper jaw 31 are slanted with respect to the teeth 4 on the lower jaw 32, malocclusion between the teeth 4 on the upper and lower jaws 31, 32 makes chewing difficult.

More specifically, taking the middle point A of the U-shaped metal wire 21 as a reference point, and the horizontal baseline 9 as a reference line, the right side of the U-shaped metal wire 21 is curved, starting from the middle point A, toward the upper law 31 (upward) by a predetermined angle θ1. Then, the end 211 is extended toward the right side 311 of upper law 31 and is curved toward the lower jaw 32 (downward) by a predetermined angle θ2. Similarly, the left side of the U-shaped metal wire 21 is curved, starting from the middle point A, toward the lower jaw 32 (downward) by the predetermined angle θ1, and then the end 212 is extended toward the left side 322 and is curved toward the upper law 31 (upward) by the predetermined angle θ2.

Thus, the U-shaped metal wire 21 is in rotational symmetry with respect to the middle point A and has a 3-dimensional recumbent S shape in front view. The predetermined curving angles θ1, θ2 are related to the vertical distance h between the two ends 211, 212 and hence related to the magnitude of a resilient restoring force that the U-shaped metal wire 21 can generate. In the present embodiment, the resilient restoring force of the U-shaped metal wire 21 is determined by three major factors: 1. the curving angles θ1, θ2; 2. the rigidity of the material; and 3. the thickness of the U-shaped metal wire 21, wherein the curving angle θ1 preferably ranges from about 0° to 45° inclusive, and the curving angle θ2 preferably ranges from about 15° to 90° inclusive.

Each tooth 4 has an outer surface 41 and a lingual surface 42. The U-shaped metal wire 21 and the plural orthodontic brackets 22 on which the U-shaped metal wire 21 is installed are mounted on either the outer surfaces 41 or the lingual surfaces 42 of a row of teeth 4. For instance, if the orthodontic device 2 is to be installed on the outer surfaces 41 of the teeth 4, the orthodontic brackets 22 will be cemented to the outer surfaces 41 of the teeth 4 respectively. Taking the middle section of the U-shaped metal wire 21 as the datum of the horizontal baseline 9, the end 211 of the U-shaped metal wire 21 is located generally below the horizontal baseline 9 and is connected to the orthodontic brackets 22 on the teeth 4 adjacent to the molars at the back end of the right side 311 of the upper jaw 31. The other end 212, which is located above the horizontal baseline 9, is fixed in position to the orthodontic brackets 22 on the teeth 4 adjacent to the molars at the back end of the left side 312 of the upper jaw 31 and thus stresses the U-shaped metal wire 21. The U-shaped metal wire 21 is secured, with the rubber bands 23 (i.e., the fasteners) and in a section-by-section manner, to the orthodontic brackets 22 cemented to the outer surfaces 41 of the teeth 4 on the upper jaw 31 and is firmly set in the grooves 221.

As the vertical distance h between the two ends 211, 212 of the U-shaped metal wire 21 is forced to decrease, the U-shaped metal wire 21 generates a resilient restoring and yet twisting force thanks to the property of the metal material itself. The resilient restoring-and-twisting force serves to adjust the row of teeth 4 on the upper jaw 31 or the lower jaw 32 to the normal tooth positions. The greater the vertical distance h between the two ends 211, 212 of the U-shaped metal wire 21 is, the stronger the resilient restoring force generated by the U-shaped metal wire 21 will be, and the harder the two ends 211, 212 of the U-shaped metal wire 21 will spring back in the two opposite directions of the vertical baseline 8 (i.e., an upward direction 81 and a downward direction 82).

It is understood that the vertical distance h between the two ends 211, 212 of the U-shaped metal wire 21 can be properly set during the manufacturing process so as to produce U-shaped metal wires 21 of different levels of resilience for use in different orthodontic treatments. For instance, it is feasible to make the U-shaped metal wire 21 in such a way that the end 212 is located below the horizontal baseline 9 while the other end 211 is above the horizontal baseline 9; thus, the U-shaped metal wire 21 is suitable for treating a slanting upper jaw 31 whose left side 312 is closer to the horizontal baseline 9 than the right side 311. In short, the relative positions of the two ends 211, 212 of the U-shaped metal wire 21 can be adjusted to provide orthodontic forces in different directions.

Figure 5:
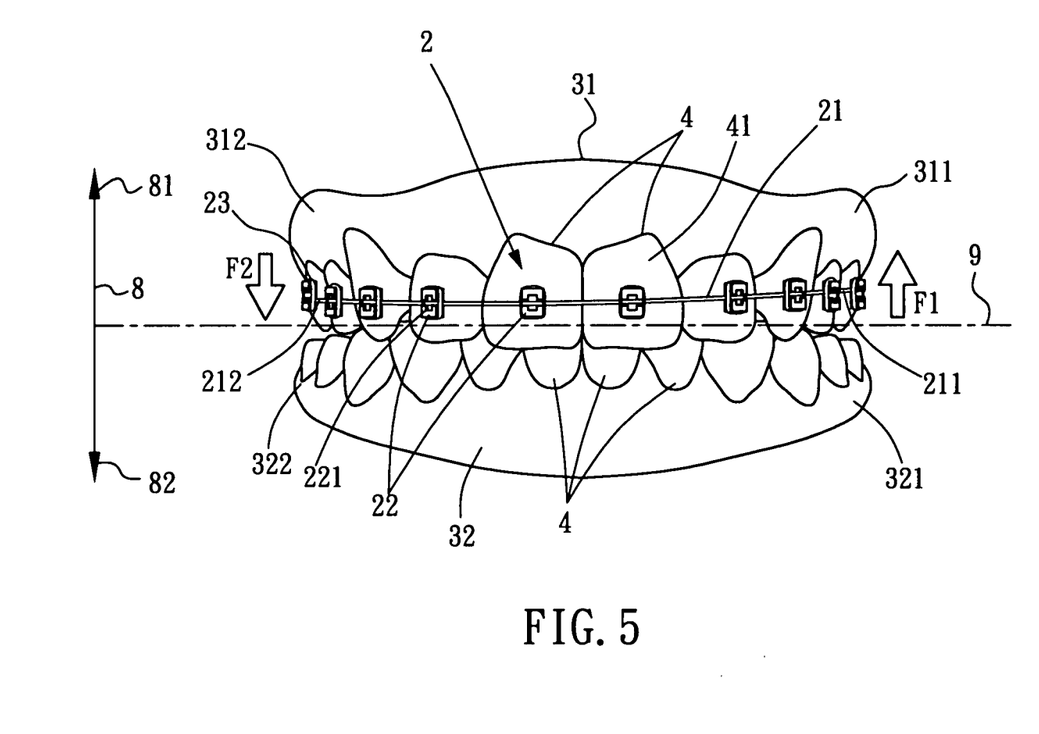
FIG. 5 is a front view of the orthodontic device in the first preferred embodiment of the present invention after the upper jaw is corrected.

More specifically, once the U-shaped metal wire 21 is fixed in position to the orthodontic brackets 22 on the outer surfaces 41 of the row of teeth 4 on the upper jaw 31, thus forcing the vertical distance h between the two ends 211, 212 of the U-shaped metal wire 21 to reduce, the two ends 211, 212 of the U-shaped metal wire 21 are vertically pressed toward the horizontal baseline 9. As a result, referring to FIG. 3 the end 211 of the U-shaped metal wire 21 generates a resilient restoring force F1 acting in the upward direction 81 of the vertical baseline 8 and thereby pushing the teeth 4 on the right side 311 of the upper jaw 31 (i.e., the side closer to the horizontal baseline 9) in the upward direction 81 of the vertical baseline 8. Meanwhile, the other end 212 of the U-shaped metal wire 21 secured to the orthodontic brackets 22 cemented to the teeth 4 on the left side 312 of the upper jaw 31 generates another resilient restoring force F2, which acts in the downward direction 82, so the teeth 4 on the left side 312 of the upper jaw 31, which are relatively far from the horizontal baseline 9, are pulled by the resilient restoring force F2 in the downward direction 82. When subjected to the two orthodontic forces F1, F2 of the U-shaped metal wire 21 for a sufficient period of time, the upper jaw 31 as a whole is moved counterclockwise to the normal position, as shown in FIG. 5. Thus, not only is normal occlusion between the upper jaw 31 and the lower jaw 32 achieved, but also the craniofacial appearance is esthetically enhanced.

Figure 6:
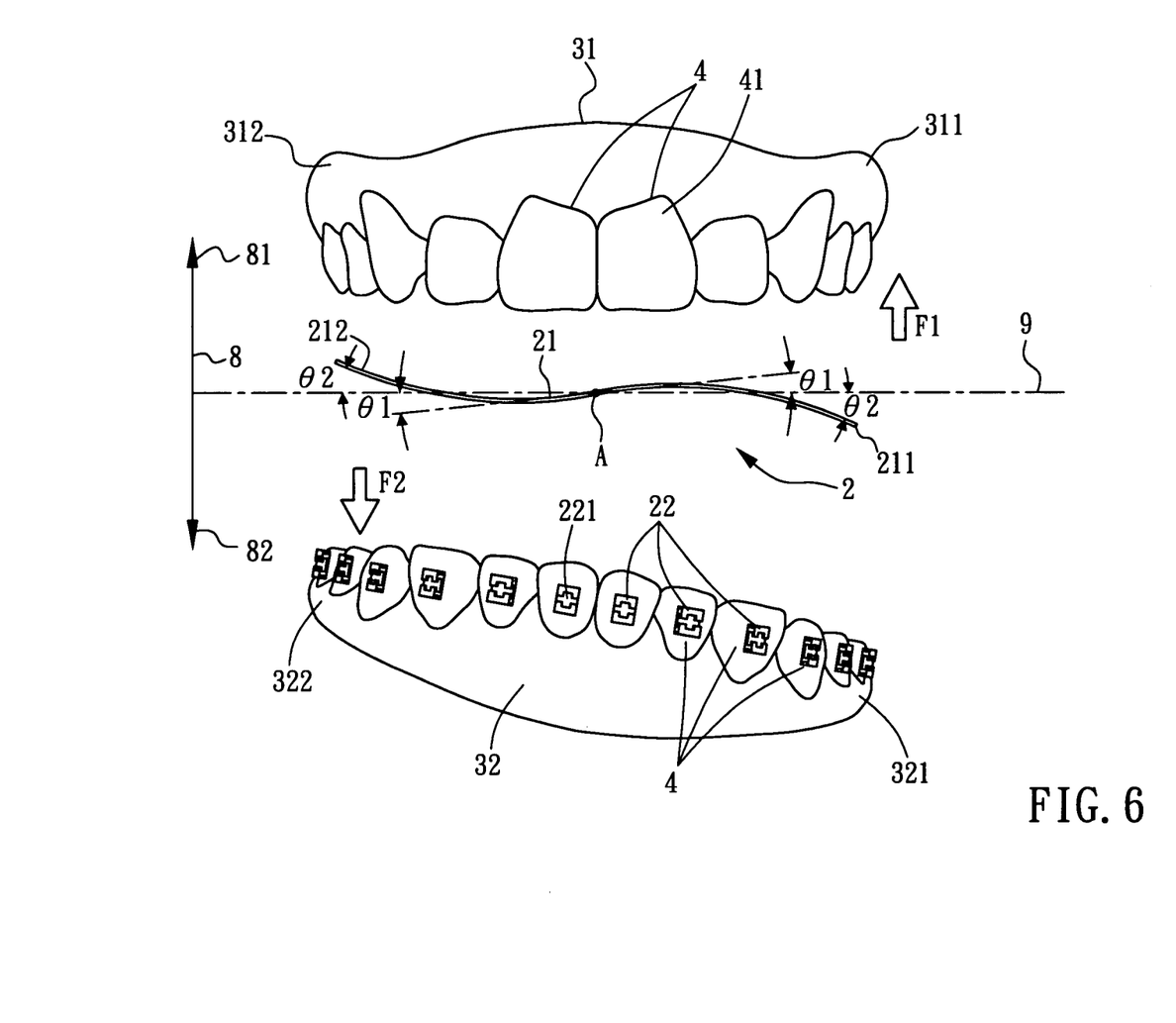
FIG. 6 is an exploded front view of the orthodontic device in the first preferred embodiment of the present invention, wherein the orthodontic device is used to correct a lower jaw.

The orthodontic device 2 of the first preferred embodiment of the present invention may also be installed alone on the teeth 4 on the lower jaw 32 and, as shown in FIG. 6, is applicable to the teeth 4 on a lower jaw 32 whose left side 322 is inclined toward the horizontal baseline 9 and therefore closer to the horizontal baseline 9 than the right side 321. After the U-shaped metal wire 21 is vertically compressed, the resilient restoring force F2 generated by the end 212 pushes the left side 322 of the lower jaw 32 in the downward direction 82, and the resilient restoring force F1 generated by the other end 211 of the U-shaped metal wire 21 pulls in the upward direction 81 the teeth 4 on the right side 321 of the lower jaw 32, which are relatively far from the horizontal baseline 9. Thus, the U-shaped metal wire 21 gradually brings the lower jaw 32 to a position capable of proper occlusion. The orthodontic device 2 may also be installed on each of the upper and lower jaws 31, 32 so as to adjust the upper and lower jaws 31, 32 to the proper positions at the same time.

The U-shaped metal wire 21 is made of stainless steel, iron, titanium, β-titanium, nickel titanium, clear material or a shape memory alloy. The orthodontic brackets 22 are metal orthodontic brackets, ceramic orthodontic brackets, crystal orthodontic brackets, self-ligation brackets or lingual orthodontic brackets.

The following paragraphs describe some other preferred embodiments of the present invention, wherein most of the elements and structures are identical or similar to those in the previous embodiment and therefore are not described repeatedly. While the same elements are identified by the same names and the same reference numerals, those similar elements are given the same names but are differentiated by an English letter suffixed to the same reference numerals.

Figure 7:
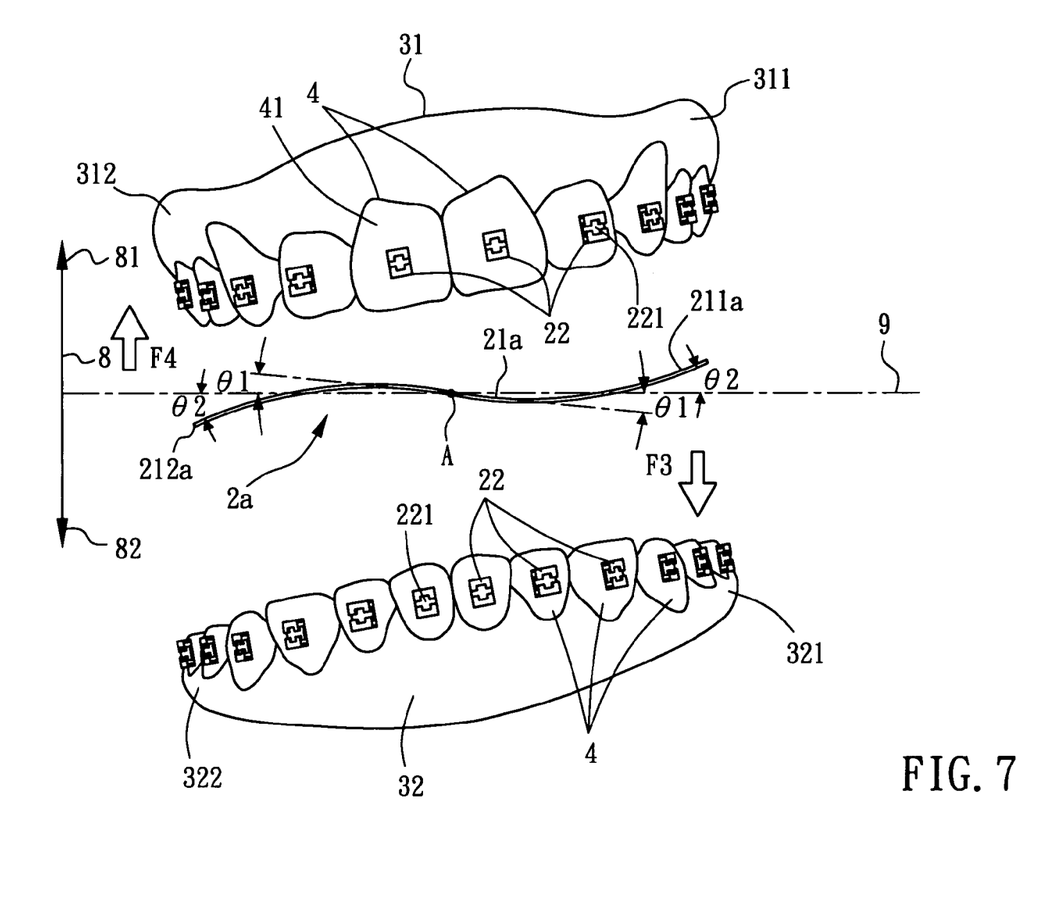
FIG. 7 is an exploded front view of an orthodontic device according to a second preferred embodiment of the present invention, wherein the orthodontic device is used to correct an upper jaw as well as a lower jaw.

Please refer to FIG. 7 for a second preferred embodiment of the present invention, which is different from the first preferred embodiment in that the end 211a of the U-shaped metal wire 21a of the orthodontic device 2a is above the horizontal baseline 9 while the other end 212a is below the horizontal baseline 9. Once the two ends 211a, 212a of the U-shaped metal wire 21a are pressed vertically toward the horizontal baseline 9, the end 211a of the U-shaped metal wire 21a generates a resilient restoring force F3 acting in the downward direction 82 of the vertical baseline 8, and the other end 212a generates a resilient restoring force F4 acting in the upward direction 81.

After the orthodontic device 2a is installed on the upper jaw 31, the teeth 4 on the right side 311 of the upper jaw 31 (i.e., the side relatively far from the horizontal baseline 9) are pulled in the downward direction 82 of the vertical baseline 8 by the end 211a of the U-shaped metal wire 21a (or more specifically by the resilient restoring force F3). Meantime, the teeth 4 on the left side 312 of the upper jaw 31, which are relatively close to the horizontal baseline 9, are pushed in the upward direction 81 by the other end 212a (or more specifically by the resilient restoring force F4).

The orthodontic device 2a is equally applicable to the teeth 4 on a lower jaw 32 whose right side 321 is inclined toward the horizontal baseline 9 and hence closer to the horizontal baseline 9 than the left side 322 (i.e., inclined in a direction opposite to that of the lower jaw 32 in FIG. 6). In that case, the resilient restoring force F3 exerted by the end 211a of the U-shaped metal wire 21a pushes the right side 321 of the lower jaw 32 in the downward direction 82, and the resilient restoring force F4 exerted by the end 212a of the U-shaped metal wire 21a pulls the left side 322 of the lower jaw 32 in the upward direction 81, so as to adjust the lower jaw 32 to a position capable of proper occlusion.

Figure 8:
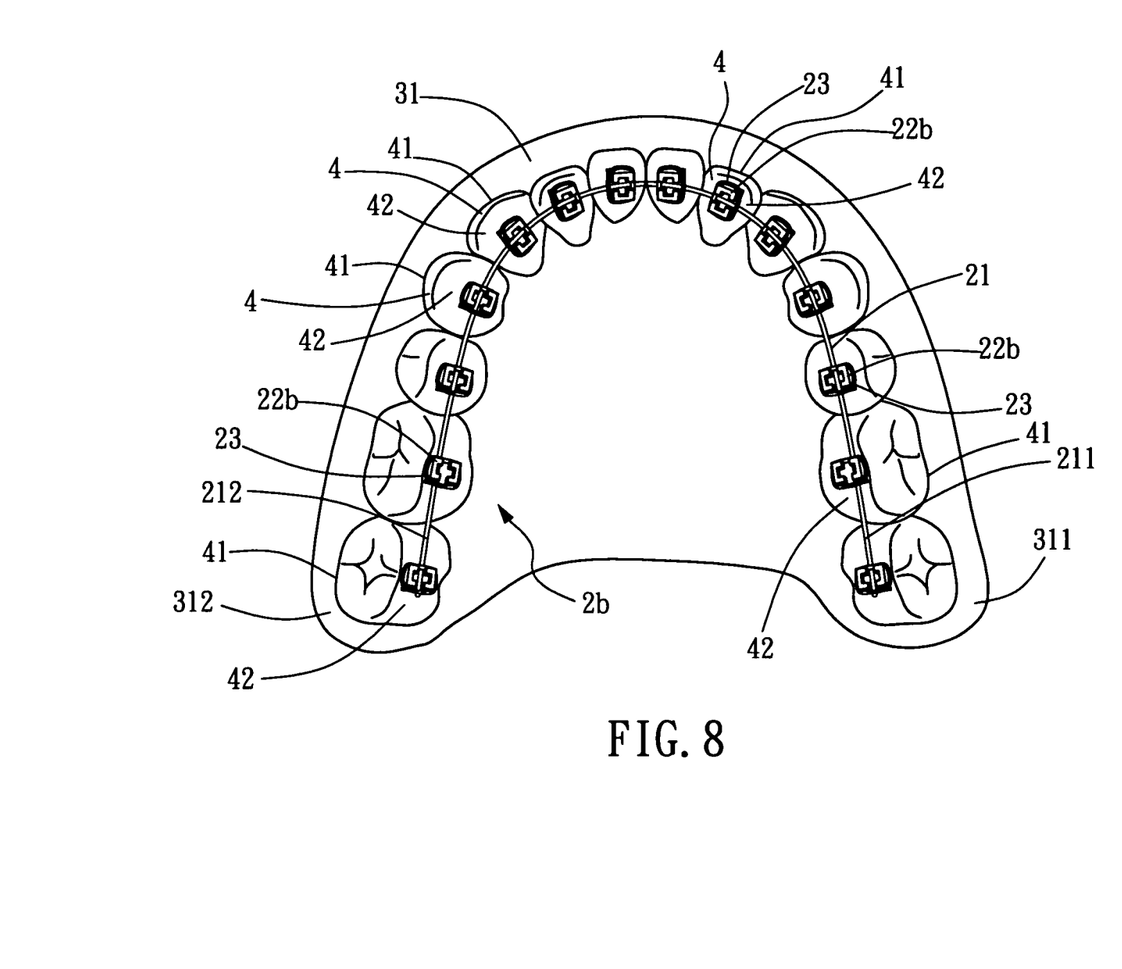
FIG. 8 shows an orthodontic device according to a third preferred embodiment of the present invention, wherein the orthodontic device is used to correct an upper jaw.

A third preferred embodiment of the present invention is illustrated in FIG. 8 and differs from the first and second preferred embodiments in that the orthodontic device 2b includes lingual orthodontic brackets 22b for securing the U-shaped metal wire 21, wherein the lingual orthodontic brackets 22b are installed on the lingual surfaces 42 of the row of teeth 4 on the upper jaw 31 or the lower jaw 32. Take an orthodontic treatment of the upper jaw 31 for example. The lingual orthodontic brackets 22b are cemented to the lingual surfaces 42 of the teeth 4 on the upper law 31 respectively. Thus, the U-shaped metal wire 21 (or the U-shaped metal wire 21a in the second preferred embodiment) and the plural lingual orthodontic brackets 22b on which the U-shaped metal wire 21 (21a) is installed are all located on the lingual surfaces 42 of the teeth 4 and hidden from view from the outside. In other words, the orthodontic device 2b will not be seen on the outer surfaces 41 of the teeth 4, and therefore the outer appearance of the teeth 4 is not affected even under orthodontic treatment.

Figure 9:
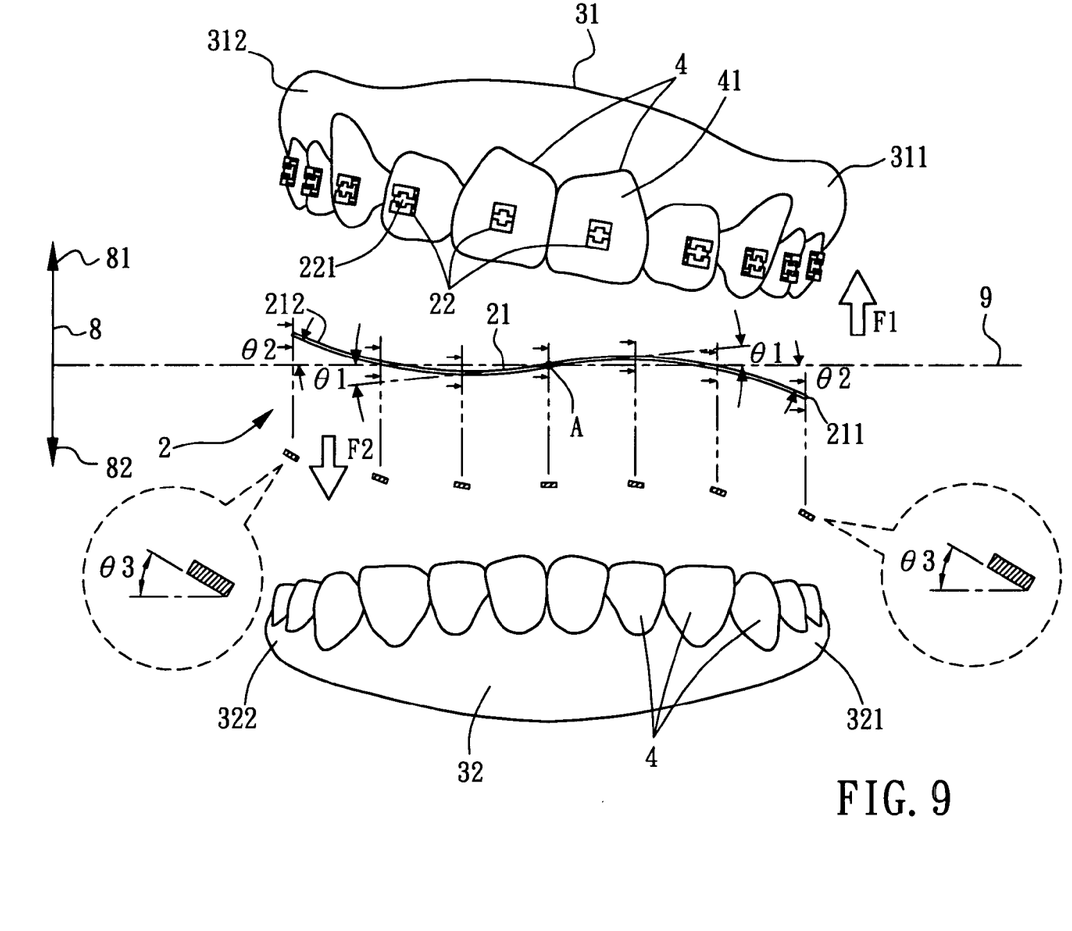
FIG. 9 is a front view and several sectional views of the U-shaped metal wire of the orthodontic device in the first preferred embodiment of the present invention.

FIG. 9 is a front view and several sectional views of the U-shaped metal wire 21 in the first preferred embodiment of the present invention. As shown in the drawing, the U-shaped metal wire 21 has a generally rectangular cross-section. Furthermore, it can be clearly seen in FIG. 9 that, in addition to the height difference between the two ends 211, 212 of the U-shaped metal wire 21 that results from the predetermined curving angles θ1, θ2, the U-shaped metal wire 21 is twisted continuously in the same direction, starting from the middle point A and proceeding to the left end 212 and the right end 211. As a result, the cross-sections of the twisted left end 212 and the twisted right end 211 of the U-shaped metal wire 21 are both inclined at a predetermined angle θ3, and because of the angle θ3 (or more specifically the twisting), the U-shaped metal wire 21 generates a linear torque, which not only determines the torsion of the U-shaped metal wire 21 but also helps increase the resilience of the orthodontic device 2. Preferably, the predetermined angle θ3 ranges from about 0° to 30° inclusive.

In a nutshell, the orthodontic device 2 of the present invention includes a resilient U-shaped metal wire 21 whose two ends 211, 212 are at different vertical heights and which is fixed in position, by means of elastic bands 23, to a plurality of orthodontic brackets 22 cemented to the tooth surfaces. The height difference between the two ends 211, 212 of the U-shaped metal wire 21 gives rise to a resilient restoring force typical the metal material, and it is this resilient restoring force that individually adjusts the row of teeth 4 on the upper jaw 31 or the lower jaw 32 to the normal tooth positions. Consequently, not only is proper occlusion between the teeth 4 on the upper and lower jaws 31, 32 achievable, but also a slightly skew face can be adjusted to a more desirable angle.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An orthodontic system, comprising a U-shaped metal wire configured to be installed on a plurality of orthodontic brackets cemented to a row of teeth, the U-shaped wire having first and second elongated sections connected by a curved section, with the first and second elongated section having a first end and a second end, respectively, opposite from the curved section, wherein said U-shaped metal wire has a middle point located at the middle between said first and second ends, wherein a horizontal plane is defined along the longitudinal length of the U-shaped wire, wherein said middle point being located on said horizontal plane, and wherein the first end is located at a vertical height lower than the horizontal plane while the second end is located at another vertical height higher than the horizontal plane when the U-shaped wire is in its preformed uninstalled configuration, wherein after the U-shaped metal wire is installed on the plural orthodontic brackets cemented to the row of teeth, the first and second ends of the U-shaped metal wire are pressed vertically toward the horizontal plane so as to generate a resilient restoring force for both pushing and pulling the row of teeth on an upper jaw or a lower jaw and thereby adjusting the teeth from an inclined alignment to a horizontal alignment.

2. The orthodontic system of claim 1, wherein the U-shaped metal wire is made of a resilient metallic material, the resilient metallic material being one of stainless steel, iron, titanium, β-titanium, nickel titanium, clear material and a shape memory alloy.

3. The orthodontic system of claim 1, wherein the U-shaped metal wire and the plural orthodontic brackets on which the U-shaped metal wire is installed are provided on one of outer surfaces and lingual surfaces of the row of teeth.

4. The orthodontic system of claim 1, wherein the U-shaped metal wire is fixed in position to the plural orthodontic brackets by one of the following: a plurality of rubber bands and a plurality of covers of self-ligation brackets.

5. The orthodontic system of claim 3, wherein the orthodontic brackets are one of metal orthodontic brackets, ceramic orthodontic brackets, crystal orthodontic brackets, self-ligation brackets and lingual orthodontic brackets, the lingual orthodontic brackets being cemented to the lingual surfaces of the teeth.

6. The orthodontic system of claim 5, wherein the U-shaped metal wire has a rectangular cross-section and is twisted continuously in the same direction, starting from the middle point of the U-shaped metal wire and proceeding to the first and second ends, such that the cross-section of the U-shaped metal wire is rotated from a horizontal position at the middle point of the U-shaped metal wire to an inclined position at each of the first and second ends, the inclined position having a predetermined angle.

7. The orthodontic system of claim 1, further including a plurality of fasteners for fixing the U-shaped metal wire in position to the plural orthodontic brackets and preventing the U-shaped metal wire from falling off.

8. The orthodontic system of claim 7, wherein the plurality of fasteners are chosen from the following: a plurality of rubber bands and a plurality of covers of self-ligation brackets.

* * * * *